United States Patent [19]

Barger et al.

[11] 4,381,591

[45] May 3, 1983

[54] METHOD OF ASSEMBLING MEDICAL FLUSHING VALVE

[75] Inventors: Larry N. Barger, Glendale; Kenneth R. McCord, Lakewood, both of Calif.

[73] Assignee: American Hospital Supply Corporation, Evanston, Ill.

[21] Appl. No.: 245,580

[22] Filed: Mar. 20, 1981

Related U.S. Application Data

[62] Division of Ser. No. 32,832, Apr. 24, 1979, Pat. No. 4,267,835.

[51] Int. Cl.³ .................. B23P 15/00; A61M 5/00
[52] U.S. Cl. ................. 29/157.1 R; 29/450; 285/235; 251/342; 604/30; 604/153; 604/252
[58] Field of Search ............ 29/157.1 R, 157 R, 450, 29/451; 285/235, 236, 260; 251/342; 128/214 E, 247, 274, 276, 350

[56] References Cited

U.S. PATENT DOCUMENTS

| 317,157 | 5/1885 | Lowrie | 285/236 |
|---|---|---|---|
| 2,706,101 | 4/1955 | Cantor | 251/342 |
| 2,832,344 | 4/1958 | Davidson | 128/766 |
| 2,946,555 | 7/1960 | Cantor | 251/342 |
| 3,111,125 | 11/1963 | Schulte | 128/350 V |
| 3,376,625 | 4/1968 | McCulloch | 29/157 R |
| 3,399,676 | 9/1968 | McLaughlin | 128/247 |
| 3,581,733 | 6/1971 | Grandjana | 128/673 |
| 3,626,959 | 12/1971 | Santomieri | 128/274 |
| 3,675,891 | 7/1972 | Reynolds et al. | 251/117 |
| 3,704,704 | 12/1972 | Gonzales | 128/274 |
| 3,882,026 | 5/1975 | McPhee | 128/214 C |
| 3,890,687 | 6/1975 | Goldberg | 29/450 |
| 3,985,140 | 10/1976 | Harris | 128/274 |
| 3,999,542 | 12/1976 | Shaw | 128/214 R |
| 4,065,093 | 12/1977 | Phillips | 251/342 |
| 4,106,675 | 8/1978 | Taylor | 128/227 |
| 4,109,837 | 8/1978 | Taylor | 251/308 |
| 4,146,082 | 3/1979 | Granger | 285/236 |
| 4,192,303 | 3/1980 | Young et al. | 128/214 F |

FOREIGN PATENT DOCUMENTS

| 451071 | 2/1913 | France | 285/236 |
|---|---|---|---|
| 182656 | 3/1922 | United Kingdom . | |

OTHER PUBLICATIONS

"Delta Flow", The Deseret Company, Catalogue No. 1280, Jun. 1978.

Primary Examiner—Daniel C. Crane
Attorney, Agent, or Firm—Roger A. Williams

[57] ABSTRACT

A valve for an arterial monitoring set which continuously supplies a small flow of parenteral liquid, such as normal saline, into a patient's artery while arterial pressure is being continuously monitored. The valve has a flow restrictor providing a normally slow continuous flow rate and an elastically distortable tube which is manually squeezable to provide a fast flush rate. The valve is convenient for one hand operation. A method for assembling the valve by twisting the tube is also disclosed.

3 Claims, 10 Drawing Figures

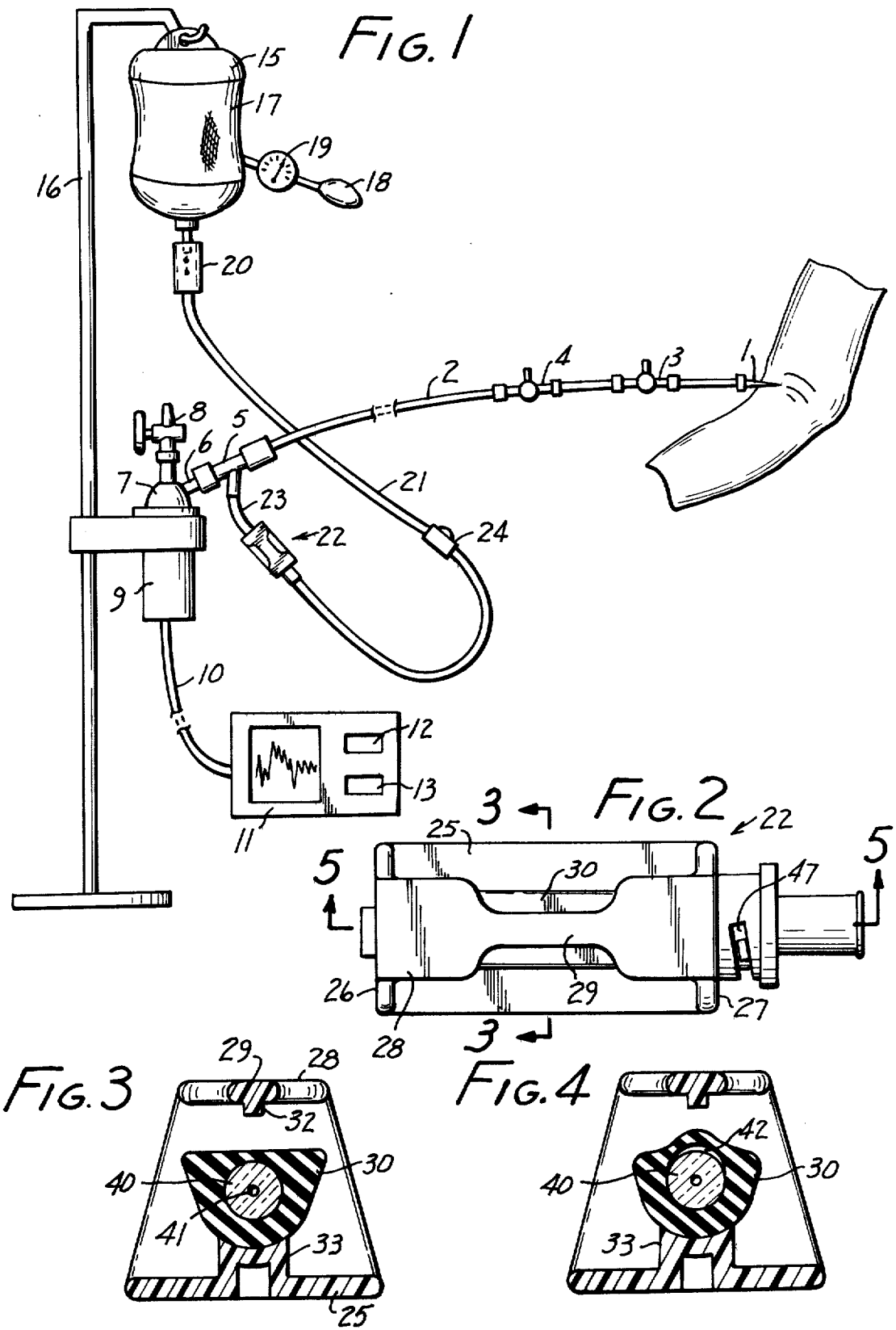

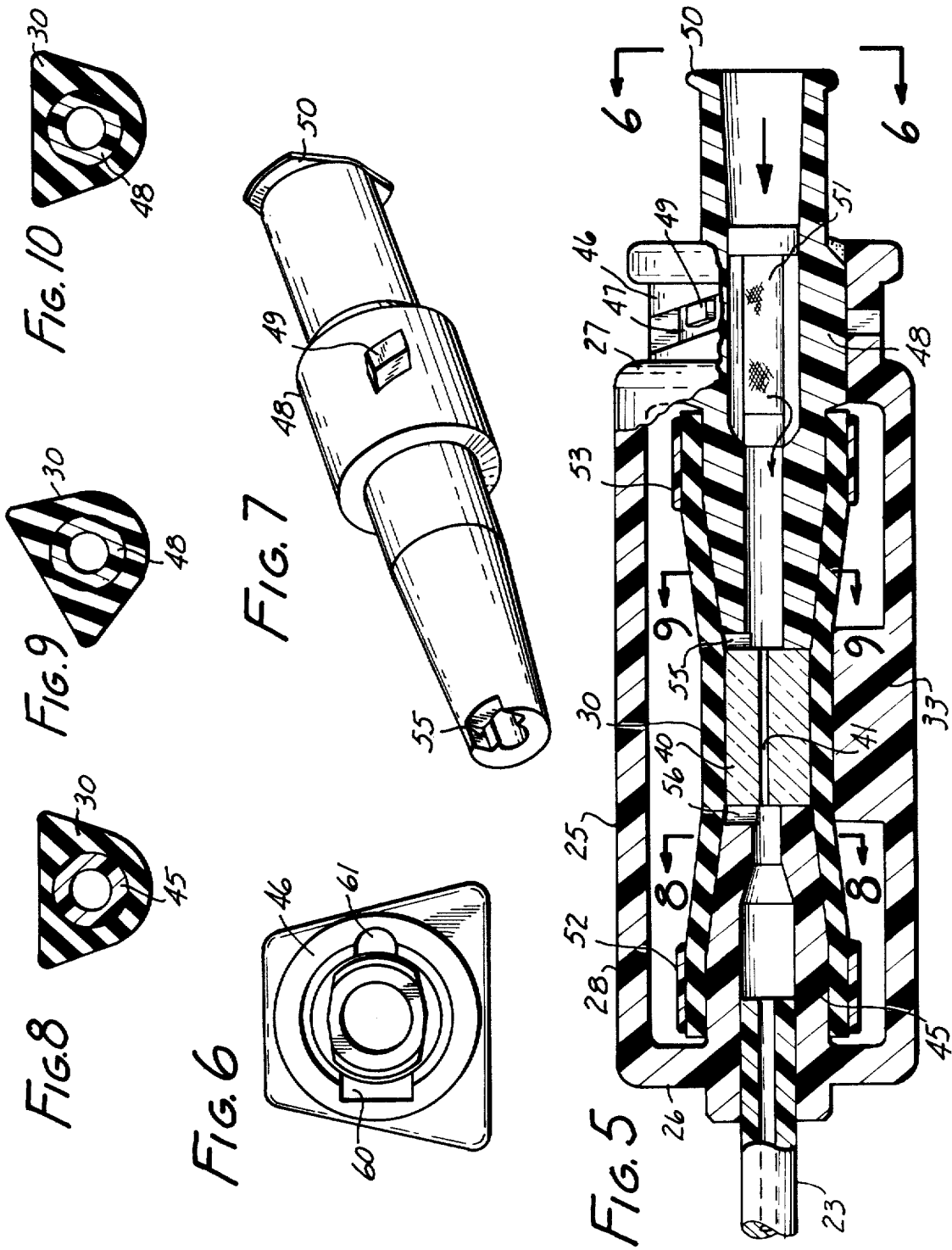

METHOD OF ASSEMBLING MEDICAL FLUSHING VALVE

This application is a division, of application Ser. No. 32,832, filed 4/24/79, now U.S. Pat. No. 4,267,835, issued 5/19/81.

BACKGROUND

U.S. Pat. No. 3,581,733 describes a system for continuously monitoring blood pressure within blood vessels and the heart. The system includes a catheter joined to a connecting tube leading to a pressure transducer that converts physical pressure signals into an electrical impulse which is then fed to a recording machine, such as an oscilloscope. As pressure readings can be seriously affected if blood should coagulate in any part of the pressure monitoring system, this patent describes continuously forcing a very slow flow of a physiological salt solution (normal saline would be an example) into the patient. This very slow flow rate is sufficient to prevent blood from backing up into the catheter and connecting tube, but is so slow that it does not cause any significant error in blood pressure reading.

Immediately after connecting the system to the patient and periodically through pressure monitoring, it becomes necessary to flush a larger amount of parenteral liquid into the patient, particularly to insure that the catheter or needle is completely free of blood. U.S. Pat. No. 3,581,733 does this flushing by a valve 18. Another type flushing valve is described in U.S. Pat. No. 3,675,891. The set up of the valve of this latter patent is described in the attached instructions for the valve made under Patent 3,675,891. This flushing valve has an elongated stem that must be pulled to actuate the valve. If the valve is not physically anchored to a rigid IV pole, transducer, etc., this operation requires two hands; i.e., one to hold the valve and one to pull the stem. Should the stem ever break off during the pulling action, the valve would be rendered useless. In addition, the valve of U.S. Pat. No. 3,675,891 includes a very large number of complicated parts including special sealing gaskets, etc.

SUMMARY OF THE INVENTION

The present invention overcomes the problems described above and provides a flushing valve with a restrictor in an elastically distortable tube. The restrictor combines with the tube to form a slow flow rate passage and the tube is distortable, such as by squeezing, to temporarily form a flush passage with a much faster flow rate. An assembly method for the valve is described in which a pair of hollow connectors are joined to the elastically distortable tube and moved into abutting contact with the flow restrictor.

THE DRAWINGS

FIG. 1 is an elevational view of a blood pressure monitoring system which includes the medical flushing valve;

FIG. 2 is an enlarged view of the flushing valve;

FIG. 3 is a sectional view taken along line 3—3 of FIG. 2 showing the valve in its unsqueezed condition or its normal slow flow rate;

FIG. 4 is a view similar to FIG. 3, but showing the valve squeezed into its temporary fast flush condition;

FIG. 5 is an enlarged view, partially in section, taken along line 5—5 of FIG. 2;

FIG. 6 is an end view taken along line 6—6 of FIG. 5;

FIG. 7 is a perspective view of a hollow connector of the valve;

FIG. 8 is a sectional view taken along line 8—8 of FIG. 5;

FIG. 9 is a sectional view taken along line 9—9 of FIG. 5 showing the position of the tube during assembly; and FIG. 10 is a sectional view similar to FIG. 9, but showing the position of the tube after assembly.

DETAILED DESCRIPTION

In FIG. 1, a system is shown for continuously monitoring blood pressure. This system has a hollow member 1, such as a needle or catheter, inserted into a patient's vein or artery. Usually blood pressure is continuously monitored from an artery because this gives a more accurate and dynamic reading of the heart function. Hydraulic pressure from the patient's artery is transmitted through a connecting tube 2 which can have ports or stopcocks, such as 3 and 4, for bleeding off blood samples or injecting medication into the patient. Tube 2 connects to a rigid T-connector 5 which is shown attached to a rigid arm 6 of a transducer pressure dome 7. It is understood that the term T-connector is used in its broad sense to also include an angled Y-connector. The transducer dome 7 includes a bleed valve 8 for use in eliminating all air from the system prior to use. It is important that no air bubbles be in the system because this can affect the hydraulic liquid pressure wave generated by the patient's heartbeat.

The pressure dome 7 of the transducer can include a diaphragm (not shown) which can respond to liquid pressure vibrations and engage electrical strain means inside a transducer body 9 to convert hydraulic liquid pressure surges into electrical impulses. Such electrical impulses are fed through a line 10 to an instrument 11 for reading the pressure fluctuations in a patient's cardiovascular system. Instrument 11 can be an oscilloscope, an electronically activated stylus, etc. If desired, the instrument 11 can have other monitoring functions, such as at 12 and 13, to monitor pulse rate, etc. in addition to blood pressure fluctuations at each heartbeat.

As explained above, the blood pressure monitoring for each heartbeat involves a liquid filled line between the patient and a diaphragm in the transducer dome. Since there is no liquid flow across the diaphragm of the transducer, there is no continuous blood flow out of the patient. This is why in U.S. Pat. No. 3,581, 733 it is necessary to very slowly force a small volume of parenteral liquid, such as normal saline, into the patient to prevent blood from backing up into the catheter and connecting tube 2 where it could coagulate over an extended period of time. Coagulated blood portions in the system can materially affect the accuracy of a pressure monitoring because such coagulated blood forms a restriction in the hydraulic pressure system. This very slow infusion of parenteral liquid (such as at 3 cc/hour) into the patient is from a container 15 supported on a pole structure 16. Preferably, container 15 is of the collapsible bag type with a pressure cuff 17 that includes a squeeze bulb 18 and pressure gauge 19. The parenteral liquid flows from container 15 through a drip chamber 20 and a connecting tube 21 to a valve shown generally at 22 which is joined by flexible tube segment 23 to the rigid T-connector 5. Flow through connecting tube 21 can be controlled by conventional roller clamp 23.

The structure of the valve shown generally at 22 and the method of assembling this valve is the subject matter of the present invention. Related co-pending co-owned applications filed on the same day as the present application are "Method of Flushing A Medical Liquid," filed Apr. 24, 1979, Ser. No. 32,830 and issued as U.S. Pat. No. 4,267,833 on May 19, 1981; "System For Flushing A Medical Liquid," filed Apr. 24, 1979, Ser. No. 32,831, now U.S. Pat. No. 4,267,834, issued May 19, 1981; and "Protector Housing For Squeezable Valve" (Design), filed Apr. 24, 1979, Ser. No. 32,971, now U.S. Pat. No. Des. 266,790, issued Nov. 2, 1982.

In FIG. 2, the enlarged view of the valve illustrates a protector housing that includes a base 25 connected to ends 26 and 27, which in turn are connected to a top 28 that has a narrow central section 29. Within the protector housing is an elastically distortable squeeze tube of rubber-like material, such as silicone. Preferably, this squeeze tube is generally transparent, or at least translucent to aid in detecting any air bubbles in the valve.

As shown in FIG. 3, the top wall has a longitudinal bracing rib 32 which extends through its longitudinal length to strengthen narrow portion 29 of the top. Bottom wall 25 has a limit lug such as cradle 33, with a concave surface, for preventing excess distortion of squeeze tube 30. Preferably, squeeze tube 30 has a generally triangular cross-sectional shape.

In FIG. 3, the valve is shown in its normal continuous slow flow rate position with the squeeze tube 30 sealingly engaging the periphery of a rigid glass flow restrictor 40 that has a bore 41 with a diameter of 0.001 to 0.004 inch. A diameter of 0.002 inch works very well and the restrictor can be made of glass tubing, such as is used for glass thermometers.

When it becomes necessary to fast flush the system of FIG. 1 with the parenteral liquid, the elastically distortable tube 30 is manually pinched through side openings of the protector housing. This causes the tube 30 to temporarily distort and create a flushing passage 42 around restrictor 40. When this is done, cradle 33 prevents undue flexure in the valve which might dislocate the restrictor. Release of the squeeze tube 30 causes it to immediately resume the FIG. 3 configuration and the predetermined slow flow rate resumed.

Perhaps the valve structure can best be understood by referring to the enlarged sectional view in FIG. 5. Here the housing's end wall 26 is integrally formed with a stationary hollow connector 45 which is joined to flexible tube segment 23. End wall 27 of the protector housing is joined to a tubular retainer 46 that has a bayonet type locking channel 47. This bayonet type lock can also be seen in FIG. 2. Fitting within tubular retainer 46 is a longitudinally movable hollow connector 48 which has a bayonet type lug 49 which engages slot 47 of retainer 46. Movable connector 49 has an internally tapered outer end and retaining ears 50 for connecting with connecting tube 21 leading from the parenteral liquid source.

As liquid is delivered from the pressurized parenteral liquid source in the system shown in FIG. 1, it flows to the left as shown by the flow arrows in FIG. 5. The liquid enters a hollow filter assembly 51 that is inside connector 48. After the liquid exits through sides of the filter as shown by the arrow, it travels to the flow restrictor 40 and the pressure forces the liquid through the restricted passage 41. The elastic tube 30 tightly seals against the external periphery of glass tube 40 and prevents any other passage of liquid other than through restricted passage 41. To firmly hold ends of the tube 30 in place, compression shrink bands 52 and 53 can be used, if desired.

When it is desired to fast flush the system of FIG. 1, the elastically distortable tube 30 is laterally squeezed between thumb and forefinger causing an upper portion of tube 30 to lift off of the periphery of glass tube 40 creating a flush passage. Thus, the liquid can flow through lateral passage 55 of connector 48, and go around restrictor 40 and enter the passage of connector 45 through its lateral passage 56.

It is important that air bubbles be eliminated from the system as they can interfere with the hydraulic pressure waves being transmitted from the patient to the transducer. For this reason, it is important that the hollow connectors 45 and 48 abuttingly engage ends of the restrictor 40 so no undue pockets are formed which could trap air bubbles. It has also been found that in cutting the glass flow restrictors 40, their length sometimes varies. To accept variable lengths of the restrictor 40, as well as eliminating any undue pockets to trap air bubbles, a special assembly method has been developed.

During assembly, the restrictor 40 is inserted into the squeeze tube and an end of tube 30 inserted on connector 45 which is fixedly joined to the protector housing. The squeeze tube has a configuration as shown in FIG. 8 at the area of assembly to connector 45. Next the right end portion of squeeze tube 30 is angularly twisted as shown in FIG. 9 and a tapered end of movable connector 48 inserted into a right end of tube 30. Lug 49 is then inserted into an entrance 60 of the bayonet type slot of the housing's retainer 46. Preferably, retainer 46 has diametrically opposed entrances 60 and 61 that are of different sizes which match with different sized lugs on diametrically opposed sides of connector 48. Thus, the connector 48 will always be oriented in the proper position so that its lateral port 55 is always at an upper part of the valve to correspond with the lateral port 56 of connector 45.

Once the connector 48 and tube 30 that has been temporarily twisted at one end with a torquing force have been assembled, lug 49 is tightened in the bayonet slot 47. The squeeze tube 30 also has a certain degree of elasticity that tends to untwist and tighten the connector 48. Thus, the bayonet type lock compressively urges the connectors 45 and 48 into compressive engagement with ends of the glass restrictor 40. If glass restrictor 40 varies slightly in length from one restrictor to the next, the bayonet structure can tolerate such variances. After the valve is assembled, the tube 30 resumes a shape generally shown at FIG. 10.

It has been found that the flushing valve of the present invention works very well when the flow restrictor is of glass, the squeeze tube is of silicone rubber, and the protective housing and hollow adapters are made of a rigid thermoplastic material.

In the above description, a specific example has been used to illustrate the invention. However, it is understood by those skilled in the art that certain modifications can be made to this example without departing from the spirit and scope of the invention.

We claim:

1. A method of assembling a medical flushing valve comprising the steps of:
   (a) sealing a restrictor inside an elastically distortable tube so the restrictor and tube combine to form a flow passage with a predetermined flow rate leaving a portion of the distortable tube extending beyond the ends of the restrictor;

(b) securing one end of the distortable tube to a first hollow connector fixed within a housing, and securing the other end of the distortable tube to a second hollow connector which is movable with respect to the housing by twisting the elastically distortable tube with a torquing force and inserting the movable second hollow connector into the twisted end of the tube; and (c) compressingly urging the first and second hollow connectors into sealing engagement with the restrictor.

2. A method as set forth in claim 1, wherein the method includes orienting the movable connector to a predetermined rotational position when attaching to the tube so that upon spiraling into sealing engagement with the restrictor a lateral port of the connector is at a particular rotational position.

3. A method as set forth in claim 2, wherein the movable connector is oriented to its particular position by orienting latch means on a bayonet type joint.

* * * * *